US011426513B2

(12) United States Patent
Tyson

(10) Patent No.: US 11,426,513 B2
(45) Date of Patent: Aug. 30, 2022

(54) IMPLANTABLE DEVICES FOR DRUG DELIVERY IN RESPONSE TO DETECTED BIOMETRIC PARAMETERS ASSOCIATED WITH AN OPIOID DRUG OVERDOSE AND ASSOCIATED SYSTEMS AND METHODS

(71) Applicant: Geoffrey Louis Tyson, Vancouver, WA (US)

(72) Inventor: Geoffrey Louis Tyson, Vancouver, WA (US)

( * ) Notice: Subject to any disclaimer, the term of this patent is extended or adjusted under 35 U.S.C. 154(b) by 0 days.

(21) Appl. No.: 15/621,449

(22) Filed: Jun. 13, 2017

(65) Prior Publication Data

US 2018/0147343 A1 May 31, 2018

Related U.S. Application Data

(60) Provisional application No. 62/427,747, filed on Nov. 29, 2016.

(51) Int. Cl.
*A61B 5/00* (2006.01)
*A61M 5/142* (2006.01)
(Continued)

(52) U.S. Cl.
CPC ....... *A61M 5/14276* (2013.01); *A61B 5/4845* (2013.01); *A61B 5/4848* (2013.01);
(Continued)

(58) Field of Classification Search
CPC ......... G16H 20/17; G06F 19/30; G06F 19/32; G06F 19/3468; G06Q 50/24;
(Continued)

(56) References Cited

U.S. PATENT DOCUMENTS 5,848,991 A 12/1998 Gross et al.
8,517,981 B2 8/2013 Zornow
(Continued)

FOREIGN PATENT DOCUMENTS

WO WO-0028892 A1 * 5/2000 ......... A61B 5/02438

OTHER PUBLICATIONS

Meng et al., "Micro- and Nano-Fabricated Implantable Drug-Delivery Systems", Therapeutic Delivery—Author Manuscript, 2012, pp. 1-10, Los Angeles, California.

*Primary Examiner* — Bhisma Mehta
*Assistant Examiner* — William R Frehe
(74) *Attorney, Agent, or Firm* — Perkins Coie LLP

(57) ABSTRACT

Implantable devices for drug delivery in response to detected biometric parameters associated with an opioid drug overdose and associated systems and methods are disclosed herein. An implantable drug delivery device configured in accordance with some embodiments of the present technology can include a housing and a reservoir configured to contain a drug for treatment of the opioid overdose. The implantable drug delivery device can also include one or more sensors each configured to detect the biometric parameters associated with the overdose. The implantable drug delivery device can further include a controller configured to receive signals related to the biometric parameter, determine whether the overdose occurred based on the signals, and, if the overdose is detected, cause the drug to be delivered to the patient.

24 Claims, 9 Drawing Sheets

(51) Int. Cl.
*A61M 5/172* (2006.01)
*G16H 20/17* (2018.01)
*A61M 31/00* (2006.01)
*A61B 5/08* (2006.01)
*A61B 5/021* (2006.01)
*A61B 5/053* (2021.01)
*A61B 5/145* (2006.01)
*A61B 5/091* (2006.01)
*A61B 5/024* (2006.01)

(52) U.S. Cl.
CPC ............ *A61B 5/686* (2013.01); *A61M 5/172* (2013.01); *G16H 20/17* (2018.01); *A61B 5/0022* (2013.01); *A61B 5/021* (2013.01); *A61B 5/024* (2013.01); *A61B 5/053* (2013.01); *A61B 5/0816* (2013.01); *A61B 5/091* (2013.01); *A61B 5/14542* (2013.01); *A61B 5/411* (2013.01); *A61M 31/002* (2013.01); *A61M 2205/33* (2013.01); *A61M 2205/50* (2013.01); *A61M 2230/20* (2013.01)

(58) Field of Classification Search
CPC ............ A61M 5/14276; A61M 5/1723; A61M 5/172; A61M 31/002; A61B 5/686
See application file for complete search history.

(56) References Cited

U.S. PATENT DOCUMENTS

| | | | |
|---|---|---|---|
| 8,695,591 B2 | 4/2014 | Olson et al. | |
| 2002/0156462 A1* | 10/2002 | Stultz | A61M 5/14276 604/288.02 |
| 2003/0088236 A1* | 5/2003 | Johnson | A61K 9/0024 604/890.1 |
| 2005/0085866 A1* | 4/2005 | Tehrani | A61N 1/3601 607/42 |
| 2005/0182389 A1 | 8/2005 | LaPorte et al. | |
| 2009/0149798 A1 | 6/2009 | Dacey, Jr. et al. | |
| 2016/0175572 A1* | 6/2016 | Crowley | A61M 31/002 604/93.01 |
| 2017/0000416 A1 | 1/2017 | Ehren | G08B 21/0453 |
| 2017/0043151 A1* | 2/2017 | Bellrichard | A61M 39/0247 |
| 2017/0172522 A1* | 6/2017 | Insler | A61B 5/4845 |
| 2018/0228969 A1 | 8/2018 | MacDonald | A61M 5/16881 |
| 2019/0125966 A1* | 5/2019 | Lee | A61B 5/4845 |
| 2020/0147307 A1* | 5/2020 | Yap | A61M 5/2033 |

\* cited by examiner

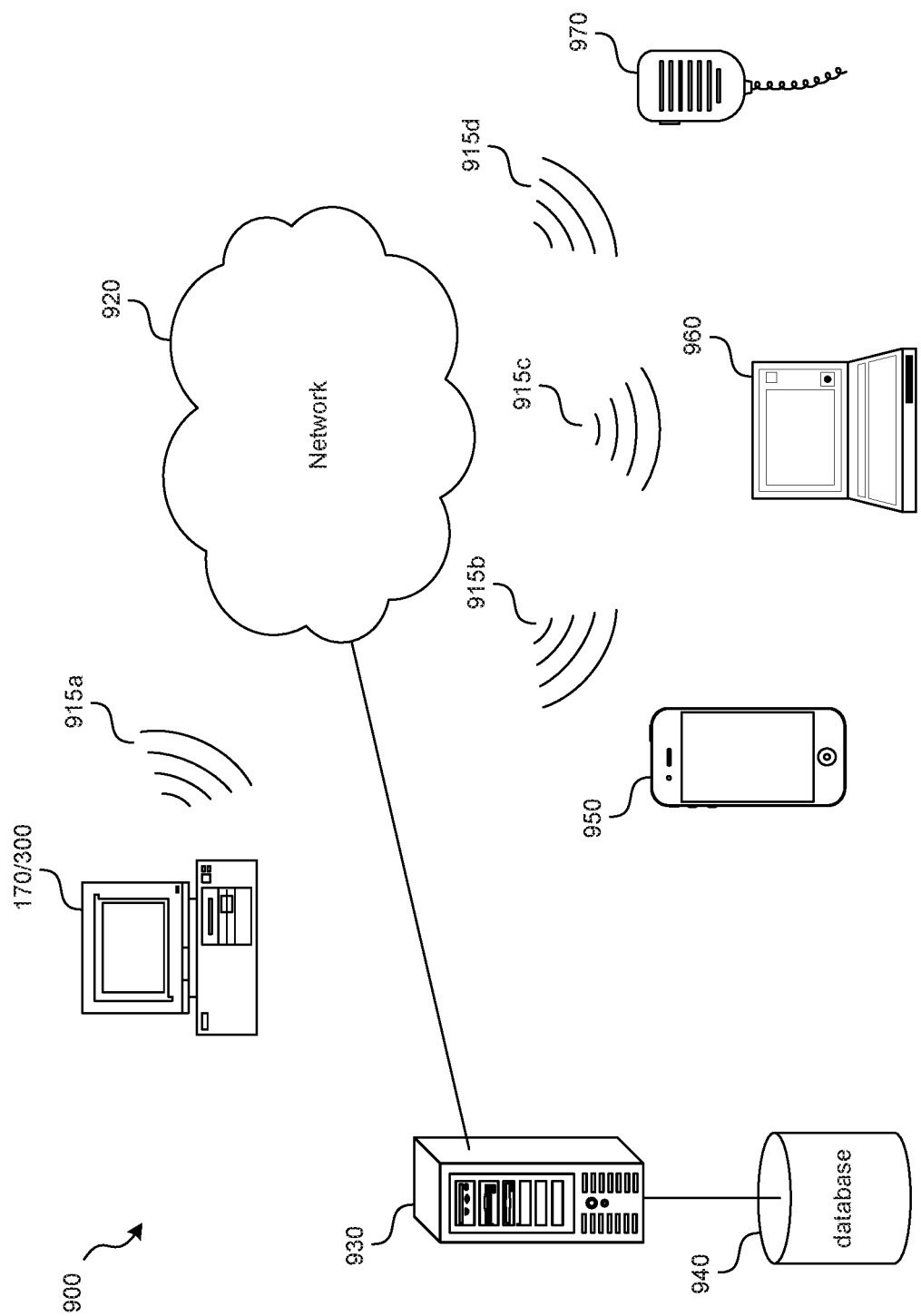

IMPLANTABLE DEVICES FOR DRUG DELIVERY IN RESPONSE TO DETECTED BIOMETRIC PARAMETERS ASSOCIATED WITH AN OPIOID DRUG OVERDOSE AND ASSOCIATED SYSTEMS AND METHODS

CROSS-REFERENCE TO RELATED APPLICATION(S)

This application claims the benefit of U.S. Provisional Patent Application No. 62/427,747 filed on Nov. 29, 2016, entitled IMPLANTABLE DEVICES FOR DRUG DELIVERY IN RESPONSE TO DETECTED BIOMETRIC PARAMETERS ASSOCIATED WITH AN OPIOID DRUG OVERDOSE AND ASSOCIATED SYSTEMS AND METHODS, which is incorporated herein by reference in its entirety.

TECHNICAL FIELD

The present technology is related to implantable devices. In particular, various embodiments of the present technology are related to implantable devices for drug delivery in response to detected biometric parameters associated with an opioid overdose.

BACKGROUND

Drug use is escalating across the world leading to rising incidences of addiction, non-fatal overdoses, and fatal overdoses. Drug overdose death rates in the United States almost tripled between 2000 and 2014. Notably, death rates from use of prescription pain killers (e.g., opioids) during this time frame have almost quadrupled. Opioids are a class of psychoactive substances derived from the opium poppy, or their synthetic analogues having similar psychoactive effects. Drugs of the opioid class include heroin and prescription pain killers such as hydrocodone, oxycodone, fentanyl, methadone, codeine, morphine, and oxymorphone, to name a few. In addition to their psychoactive properties, opioids cause respiratory depression.

Approximately 24 million Americans reported non-medically (e.g., without a prescription) use of prescription pain killers between 2002 and 2014. In 2014 alone more than 86,000 people in the United States died from a drug overdose. Of these, 18,893 deaths were caused by prescription opioids and 10,574 by heroin. In 2011, 366,181 emergency department visits were linked to misuse or abuse of prescription pain killers. Notably, the rise in overdoses and overdose related-deaths parallels the increase in the sale of prescription pain killers. In 2013 alone, 207 million prescriptions for opioid-based pain killers were dispensed by pharmacies in the United States.

Naloxone, an opioid receptor antagonist, reverses the effects of an opioid overdose and can be administered by intravenous, intramuscular, subcutaneous, and intranasal routes. If administered before respiratory depression becomes fatal, naloxone can save a person's life. Some municipalities have provided naloxone to people likely to witness an opioid overdose (such as family, friends, sponsors, etc.), which has prevented some fatalities. For example, between 1996 and 2010, at least 188 opioid overdose prevention programs distributed naloxone within 15 states and in the District of Columbia. Collectively, these programs trained and provided naloxone to 53,032 lay persons (non-emergency responders) who reversed 10,171 drug overdoses. However, because many overdoses are not witnessed, emergency responders and lay persons supplied with naloxone are not notified in time of the emergency and often do not arrive before fatalities occur. Accordingly, despite the increased availability of naloxone there are still a high number of fatal overdoses.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical or at least generally similar or analogous components or features.

FIG. 9 is a diagram schematically illustrating an overview of an environment in which some implementations of the present technology can operate.

DETAILED DESCRIPTION

Figure 1:
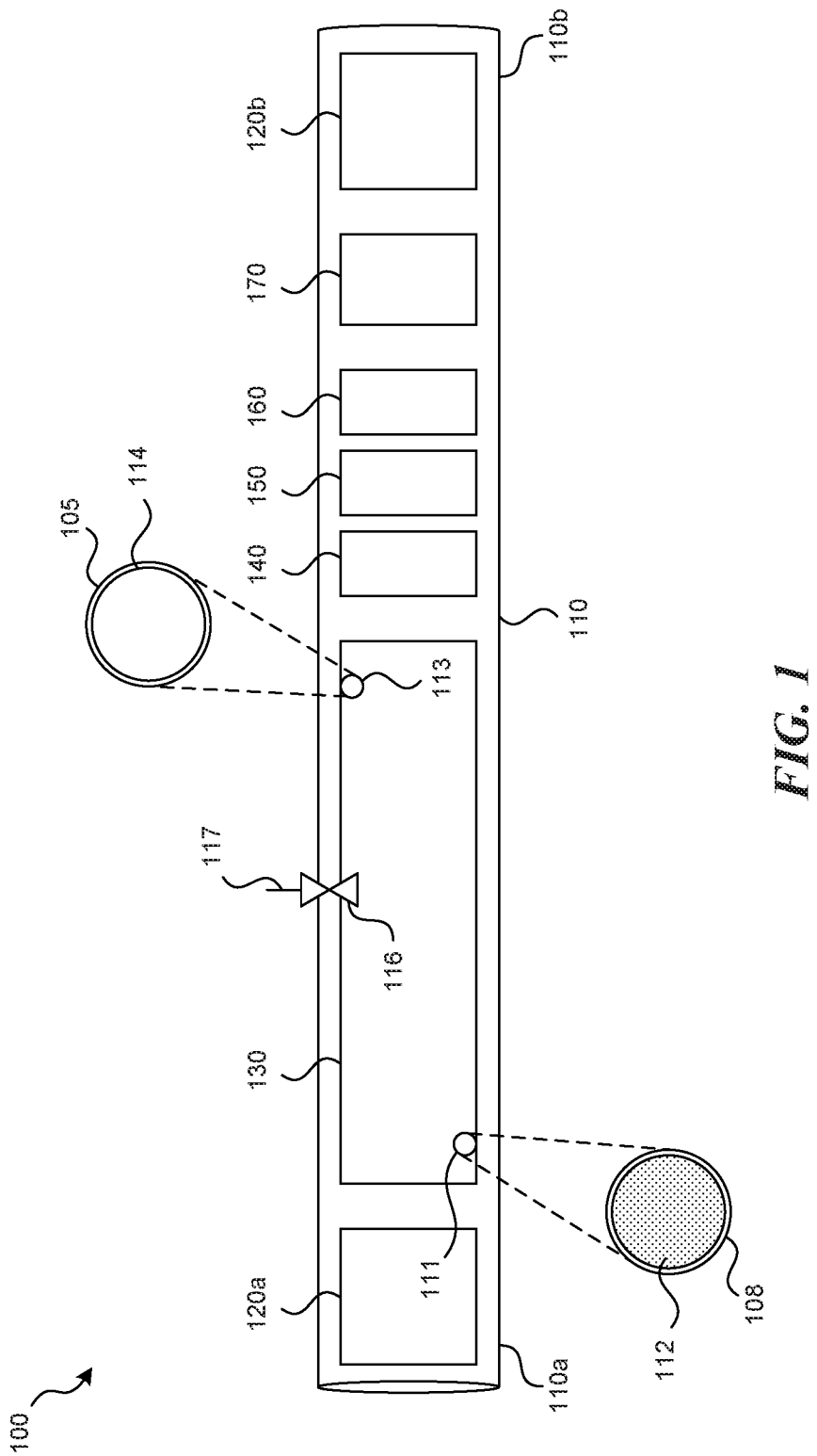
FIG. 1 is a schematic view of an implantable drug delivery device configured in accordance with an embodiment of the present technology.

Implantable drug delivery devices, methods, and systems in accordance with embodiments of the present technology include one or more sensors configured to detect a biometric parameter of the patient (e.g., respiration rate) and a reservoir configured to contain a drug (e.g., one or more drugs for treating an opioid overdose). In certain embodiments, the drug delivery device also includes a controller configured to receive signals from the sensors related to the biometric parameter. The controller can be configured to determine whether the overdose has occurred based on the received signals and, if the overdose occurred, cause the drug in the reservoir to be delivered to the patient. Specific details of several embodiments of the present technology are described herein with reference to FIGS. 1-9.

Although many of the embodiments are described with respect to devices, methods, and systems for treating an opioid overdose, other applications and other embodiments in addition to those described herein are within the scope of the present technology. For example, at least some embodiments of the present technology may be useful for delivering a drug for treatment of other acute events requiring immediate pharmacotherapy, such as drug overdose from non-opioid class drugs such as benzodiazepines, an allergic reaction, a heart attack, or the like.

In addition, a person of ordinary skill in the art will understand that embodiments of the present technology can have configurations, components, and/or procedures in addition to those shown or described herein. Moreover, these and other embodiments can be without several of the configurations, components, and/or procedures shown or described herein without deviating from the present technology.

As used herein, the terms "lateral" and "medial" define a position or direction with respect to a human (e.g., location of the device as implanted or as will be implanted). The terms, "distal" and "distally" refer to a position distant from or in a direction away from the device. The terms "proximal" and "proximally" refer to a position near or in a direction toward the device.

As used herein, the term "opioid" and "opioids" include psychoactive substances derived from the opium poppy, or their synthetic analogues having similar psychoactive effects. Opioids include prescription pain relief drugs, such as hydrocodone, oxycodone, fentanyl, methadone, codeine, morphine, and oxymorphone as well as drugs such as heroin.

Finally, the headings provided herein are for convenience only and should not be construed as limiting the subject matter disclosed.

I. Implantable Drug Delivery Devices and Associated Methods for Treatment

Naloxone (also known as Narcan®) is the current standard of care for treating an opioid overdose. As an antagonist, naloxone counteracts the effects of opioids, such as life-threatening depression of the central nervous and respiratory systems. Although traditionally administered by emergency responders, naloxone can be administered by minimally trained laypeople. As such, naloxone is a viable treatment with potential wide-spread application for people who may overdose on heroin and/or other opioids. While naloxone availability across the United States has increased to include laypersons, opioid overdose deaths continue to rise nationwide for several reasons. First, many overdoses occur in private while the person is alone. In these cases, the person suffering from the overdose may not be able to request emergency assistance. Second, witnesses may fail to request emergency assistance while naloxone could be effective because they don't realize the person is suffering an overdose or they underestimate the severity of the overdose. Third, emergency assistance may not arrive in time to save the person or naloxone may not be available to those providing assistance.

The present technology includes several embodiments of implantable drug delivery devices having a reservoir and one or more sensors. These implantable drug delivery devices are configured to sense one or more biometric parameters of the patient associated with an opioid overdose. In addition, these devices include a controller configured to analyze the biometric parameters to determine if the opioid overdose has occurred. If the opioid overdose is determined to have occurred, naloxone is automatically released from the reservoir and into the patient in accordance with the present technology.

FIG. 1 is an isometric view of an implantable drug delivery device 100 configured in accordance with an embodiment of the present technology. The implantable drug delivery device 100 includes a housing 110 having a first portion 110a (e.g., a medial portion) and a second portion 110b (e.g., lateral portion). The housing 110 can be sized and shaped for placement into a location of a patient that one or more of the biometric parameters can be measured. For example, the device can be anteriorly, laterally or posteriorly placed subcutaneously on the patient's chest wall, such as within the subclavicular space. Advantages of placing the device in the subclavicular space include ease of access, established surgical techniques for placement, and relatively close proximity to the patient's central circulation for rapid delivery of the drug to the brain. In other embodiments, the device can be placed near the patient's central circulation, proximal to a lung, near a brainstem, or other location within sufficient proximity to the patient's central circulation. In these embodiments, the housing 110 can be a cylinder having a diameter of about 0.25 inches to about 0.5 inches and a length of about 2 inches to about 6 inches, a polyhedron having a width of about 0.25 inches to about 0.5 inches, a length of about 2 inches to about 6 inches, and a depth of about 0.25 inches to about 0.5 inches, or one or more other suitable sizes and shapes. In addition, the size and shape of the housing 110 can further be selected such that the implantable drug delivery device 100 is suitable for delivery into the patient using a needle (e.g., 7, 8, 9, or 10 gauge), trocar, introducer or dilator. In other embodiments, the size and shape of the housing 110 can further be selected for delivery through an incision.

The implantable drug delivery device 100 includes one or more sensors, such as a first sensor 120a and a second sensor 120b (collectively "sensors 120"), configured to sense one or more biometric parameters of the patient in the embodiment illustrated in FIG. 1. The sensors 120 include one or more contacts (not shown) for sensing the biometric parameter of the patient. The biometric parameters can include respiration rate (e.g., peak to peak), tidal volume, blood oxygen level, ratio of $CO_2$ and $O_2$, heart rate, blood pressure, or other biometric parameters suitable for determining if the opioid overdose has occurred. An overdose can be determined by analysis of the biometric parameters in accordance with the present technology. The sensors 120 can be impedance sensors, inductor-capacitor oscillators, or other sensors suitable for sensing one or more the biometric parameter(s). In embodiments of the implantable drug delivery device 100 having additional sensors, such as a third sensor and a fourth sensor, the additional sensors can be configured to detect a different biometric parameter from the first sensor 120a and the second sensor 120b. For example, the first sensor 120a and the second sensor 120b can be configured to sense the patient's respiration rate, while a third sensor and a fourth sensor (not shown) can be configured to detect the patient's heart rate. Likewise, where the sensors 120 include more than one contact, the sensors 120 can be configured to sense more than one biometric parameter with certain contacts sensing a first biometric parameter (e.g., respiration rate) and other contacts sensing a second biometric parameter (e.g., heart rate).

In the illustrated embodiment, the sensors 120 are each operatively coupled to a power source 140 wirelessly or by a pair of lead wires carried by the housing 110 (not shown). The power source 140 can be a battery, an accelerometer, or other type of power source suitable for providing power to the sensors 120. Although the power source 140 and the lead wires are carried by the housing 110 in FIG. 1, the power source 140 can be located externally of the housing 110, such as on the patient's wrist, skin, hip, or other suitable location. In these embodiments, the sensors can be wirelessly coupled to the power source 140.

In the embodiment shown in FIG. 1, the first sensor 120a is at the medial portion 110a of the housing 110 and the second sensor 120b is at the lateral portion 110b. In other embodiments, the sensors 120 can be at other portions of the housing. For example, the first sensor 120a can be at the lateral portion 110b and the second sensor can be at the medial portion 110a of the housing 110, or the sensors 120 can be at other portions of the housing, such as an intermediate portion.

As illustrated in FIG. 1, the implantable drug delivery device 100 also includes a reservoir 130 configured to contain a drug, such as a pharmaceutical composition for treating an opioid overdose that can include an opioid receptor antagonist (e.g., naloxone). The reservoir 130 is carried by the housing 110. In some embodiments, the reservoir 130 is a fluid tight compartment or container enclosed within the housing 110, but in other embodiments the reservoir 130 is a container mounted to an outer surface of the housing 110. The reservoir 130 can be sized and shaped to carry a single dose of naloxone, in volumes from about 0.5 cc to about 5 cc, such as about 0.5 cc, about 0.75 cc, about 1 cc, about 1.5 cc, about 1.75 cc, 2 cc or about 5 cc.

The reservoir 130 can further include an outlet port 111 that extends through the housing 110 fluidly coupling the reservoir 130 to the patient. As shown in exploded view 108, the outlet port 111 can be coupled to a drug release mechanism 112, such as a membrane or a valve, to prevent release of the drug carried by the reservoir 130 until the opioid overdose occurs. The drug release mechanism 112 can be a passively driven mechanism or an actively driven mechanism. For example, the drug release mechanism 112 can be a peristaltic mechanism, a plunger or piston driven by a spring or motor, a pressurized gas expansion mechanism, an actuation mechanism, an electrochemical dissolution mechanism, an electrothermal degradation mechanism, a thermoresponsive hydrogel valve mechanism, a thermal energy bubble mechanism, a combination thereof, or another mechanism suitable for embodiments of the implantable drug delivery devices.

In an alternative embodiment, the device can include a pump 116 and/or a needle 117. The pump 116 can be an active pump, such as an electrostatic pump, a piezoelectric pump, an electrochemical pump, a thermal pump, or a combination thereof; a passive pump, such as an osmotic pump, a spring-powered pump; a combination thereof, or other pump suitable for embodiments of the implantable drug delivery devices. Regardless of the type, in one embodiment the pump 116 is coupled to the needle 117 to drug in the reservoir 130 to the patient through the needle 117. In other embodiments, the pump 116 can be fluidly coupled to a different structure, such as the outlet port 111, to pressurize the reservoir 130 and thereby deliver the drug in the reservoir 130 to the patient via the outlet port 111.

In the illustrated embodiment, the implantable drug delivery device 100 further includes an inlet port 113. As shown in exploded view 105, the inlet port 113 is coupled to a seal 114 to prevent release of the drug carried by the reservoir 130. The seal 114 can configured to allow the reservoir 130 to be re-filled with the drug once at least some of the drug has been delivered to the patient. For example, the seal 114 can be a re-sealable membrane.

The implantable drug delivery device 100 optionally also includes a signal emitter 150 carried by the housing 110. The signal emitter 150 is configured to emit a signal when the drug is released from the reservoir 130, such as an audible signal, a visual signal, or both. When configured to emit an audible signal, the signal emitter 150 is operatively coupled to a sound generator and speaker, both of which may be carried by the housing 110 or an external monitor/controller wirelessly coupled to the device 100. When configured to emit a visual signal, the signal emitter 150 is operatively coupled to a light, such as an LED, which may be carried by the housing 110 or an external monitor/controller wirelessly coupled to the device 100. The signal emitted by the signal emitter 150 can alert a conscious patient that a dose of the drug contained in the reservoir 130 has been released in response to an overdose or due to a non-overdose related change in the biometric parameter(s).

The implantable drug delivery device 100 illustrated in FIG. 1 optionally includes a signal transmitter 160 configured to transmit a transmitted signal when the drug is released from the reservoir 130, such as a wirelessly transmitted signal. In these embodiments, the wirelessly transmitted signal can be a telecommunications signal, a global positioning system signal, an audible signal, a visual signal, or a combination thereof, that is sent to an external device including a computer, phone, radio, or other suitable device for receiving the transmitted signal. In other embodiments, the signal transmitter 160 is external from the housing. The signal transmitted by the signal transmitter 160 alerts another party, by way of the external device, that a dose of the drug contained in the reservoir 130 has been released to the potentially unconscious patient. In this way, the patient may receive emergency medical attention despite being unconscious. In further embodiments, the implantable drug delivery device 100 does not include the signal transmitter 160.

As illustrated in FIG. 1, the implantable drug delivery device 100 includes a controller 170, either in the housing 110 or external to the housing 110. The controller 170 can include a converter, a microprocessor, a transmitter, and a receiver (not shown in FIG. 1). The controller 170 is operatively coupled to the power source 140 and configured to instruct the power source 140 to supply power to the sensors 120. The controller 170 is also operatively coupled to the first sensor 120a and the second sensor 120b and configured to convert signals detected by the sensors 120 at the converter and receive the converted signals at the receiver. In addition, the controller 170 is operatively coupled to the outlet port 113 and/or the pump 116 and configured to activate the drug release mechanism coupled to the outlet port 111 to remove at least a portion of the membrane and/or activate the pump 116 if an overdose is detected. Moreover, the controller 170 is operatively coupled to the signal emitter 150 and the signal transmitter 160. The controller 170 is configured to instruct the signal emitter 150 to emit the emitted signal and instruct the signal transmitter 160 to transmit the transmitted signal when an opioid overdose occurs.

In the illustrated embodiment, the sensors 120, the reservoir 130, the power source 140, the signal emitter 150, the signal transmitter 160, and the controller 170 are integral components of the housing 110. In other embodiments, only the sensors 120, the reservoir 130, the power source 140, and the controller 170 are integral components of the housing 110. In additional embodiments, the device 100 may not include the power source 140 integrated in the housing 110 such that only the sensors 120, the reservoir 130, and the controller 170 are integral components of the housing 110. In this embodiment, the power source can be external to the patient and transmit power via an alternating magnetic field.

In further embodiments, only the reservoir 130 and the controller 170 are integral components of the housing 110.

Figure 2:
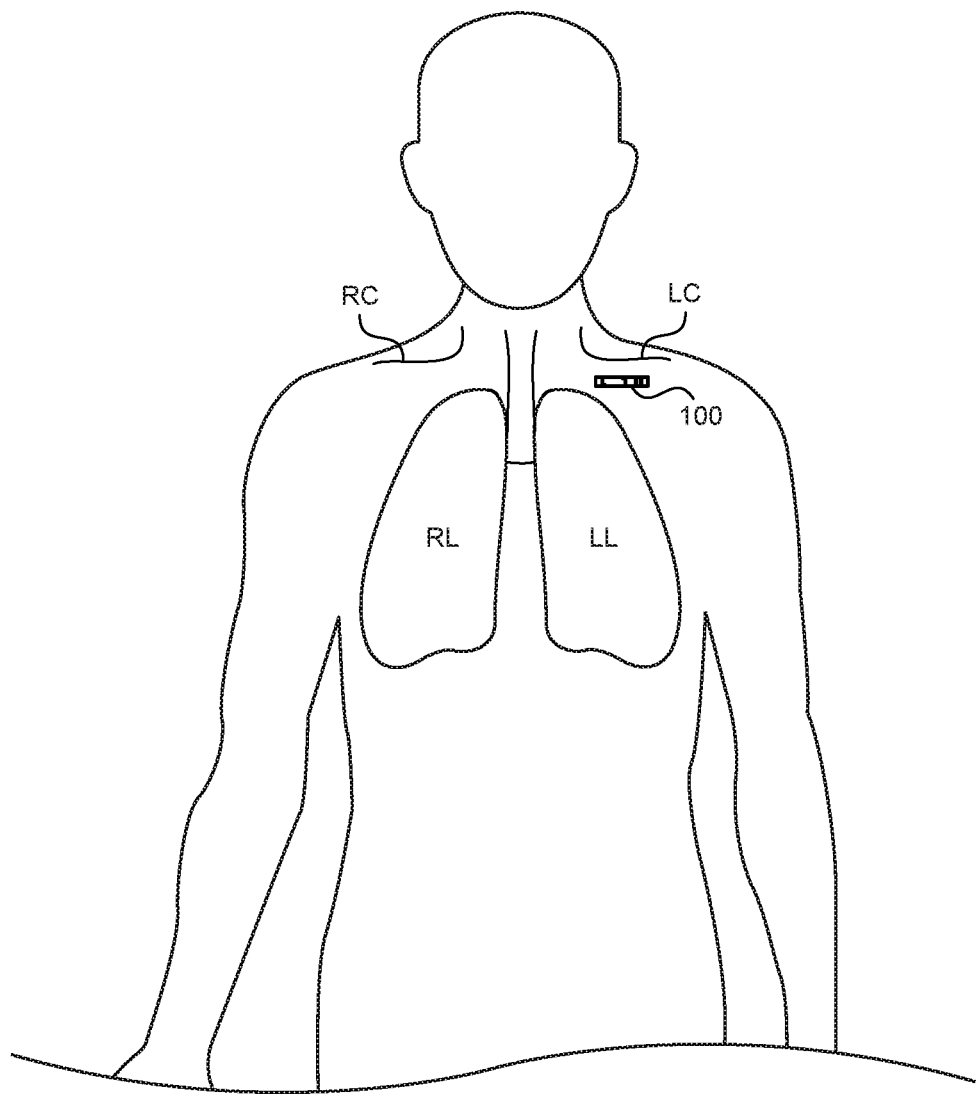
FIG. 2 is an anatomic view of the implantable drug delivery device of FIG. 1 implanted in a subclavicular space of a human in accordance with an embodiment of the present technology.

FIG. 2 is an anatomic view of the implantable drug delivery device 100 illustrated in FIG. 1 implanted within the subclavicular space of a patient in accordance with an embodiment of the present technology. In the illustrated embodiment, the drug delivery device 100 is implanted into the patient's subclavicular space through an incision. In other embodiments, the implantable drug delivery device 100 can be implanted through a needle (e.g., 7, 8, 9, or 10 gauge), trocar, introducer or dilator inserted subcutaneously into the patient's subclavicular space. In other embodiments, the implantable drug delivery device 100 can be implanted in other locations suitable for detecting the biometric parameter(s) that the sensors 120 are configured to detect, such as those described above with reference to FIG. 1. In the illustrated embodiment, the device 100 is implanted inferior to the left clavicle (LC) and external to the left lung (LL) and impedance sensors 120 are configured to detect the patient's respiratory rate.

In other embodiments, a similarly configured implantable drug delivery device 100 can be implanted in the patient's subclavicular space inferior to the right clavicle (RC) and external to the right lung (RL).

Figure 3:
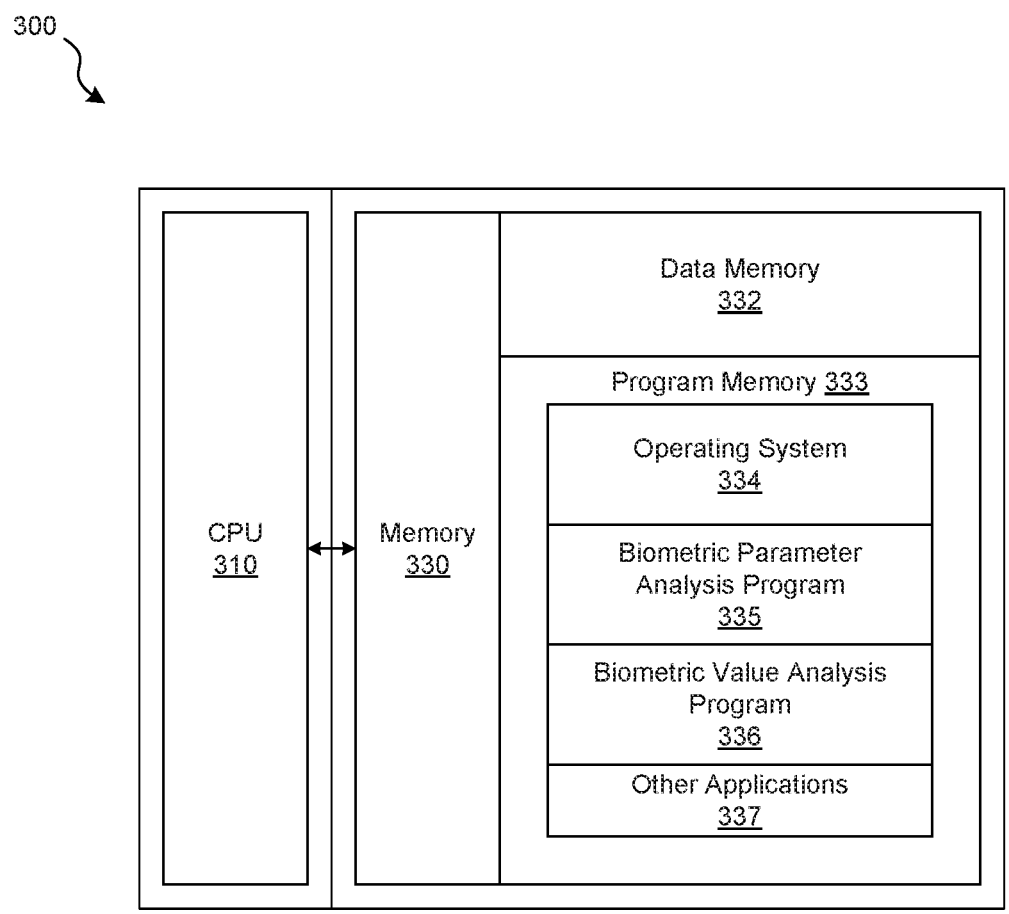
FIG. 3 is a schematic view illustrating components of a device in accordance with an embodiment of the present technology.

FIG. 3 is a block diagram illustrating an overview of an embodiment of a controller 300 on which some implementations of the present technology may operate. The controller 300 can include components or modules for analyzing detected biometric parameter(s), determining a biometric value from the analyzed biometric parameter(s), comparing the biometric value against a threshold biometric value, and, based on the comparison, determining whether the drug overdose occurred. If a drug overdose occurred, one or more components of controller 300 communicate with the release mechanism coupled to the outlet port 112 (FIG. 1) and/or the pump 116 (FIG. 1) to release the drug from the reservoir 130 (FIG. 1). In addition, hardware components of controller 300 can be configured to determine a trend in the patient's biometric parameter(s) and/or biometric value(s).

The controller 300 can include, for example, one or more input devices for providing input to a central processing unit 310 ("CPU"; processor) and/or notifying the CPU 310 of actions to perform. The CPU 310 is configured to communicate with the release mechanism coupled to the outlet port 112, the pump 116, a network node (not shown), a server (FIG. 9), and/or a combination thereof. The input devices, for example, can be configured to receive signals from the first sensor 120a and the second sensor 120b described with reference to FIG. 1. The output devices include, for example, a converter of controller 300 for converting signals received from the sensors 120 into a medium readable by the CPU 310. The communication devices include, for example, a transmitter of controller 300 for transmitting signals to activate the release mechanism coupled to the outlet port 112 and/or the pump 116 when the patient has overdosed.

In addition, controller 300 can execute embodiments of blocks 410, 420, 430, 440, 450, and 460 of method 400 described in further detail below with respect to FIG. 4. In order to execute these embodiments, the CPU 310 can access a memory 330 (e.g., computer readable medium) including data memory 332 that stores the data sensed by one or more of the sensors 120. The stored data can include patient data, algorithms related to biometric parameter analysis and/or biometric value analysis, configuration data, settings, etc. The patient data includes data related at least to baseline measurements of biometric parameters and/or biometric values of the patient and trend measurements of the same. The baseline measurements are determined from the patient when the patient is not under the influence of an opioid or other type of drug or circumstance which could alter the baseline biometric parameters. The trend measurements are determined while the device 100 is implanted in the patient and can be used in place of or in addition to the threshold biometric values.

The memory can also include program memory 333 for storing programs and software, such as an operating system 334, a biometric parameter analysis program 335, a biometric value analysis program 336, and other applications 337. The biometric parameter analysis program 335, for example, can include one or more algorithms for analyzing various indices related to one or more biometric parameters or other information related to a potential opioid overdose. The biometric value analysis program 336, for example, can include one or more algorithms for determining a biometric value corresponding to each of the analyzed biometric parameters. The biometric value can be determined by normalizing the one or more biometric parameters such as by removing outliers and calculating an average. For example, the biometric values can include a respiratory rate biometric value, a tidal volume biometric value, and/or a respiration biometric volume indicative of both the patient's respiratory rate and tidal volume. In addition, the biometric value analysis program 336 can compare the biometric value against a threshold biometric value to determine if a drug overdose has occurred. The threshold biometric value can be determined from one or more baseline biometric parameters prior to implanting the device 100 in the patient or after the device has been implanted. In addition, other applications 337 can include a trend analysis program for analyzing trend measurements and comparing the trend measurements against the biometric parameters and/or the threshold biometric values. The biometric parameters, threshold biometric values and/or the trend parameters related to each biometric parameter are stored in data memory 332. Any of the stored data can be provided to program memory 333 or any element of the device 300.

Figure 4:
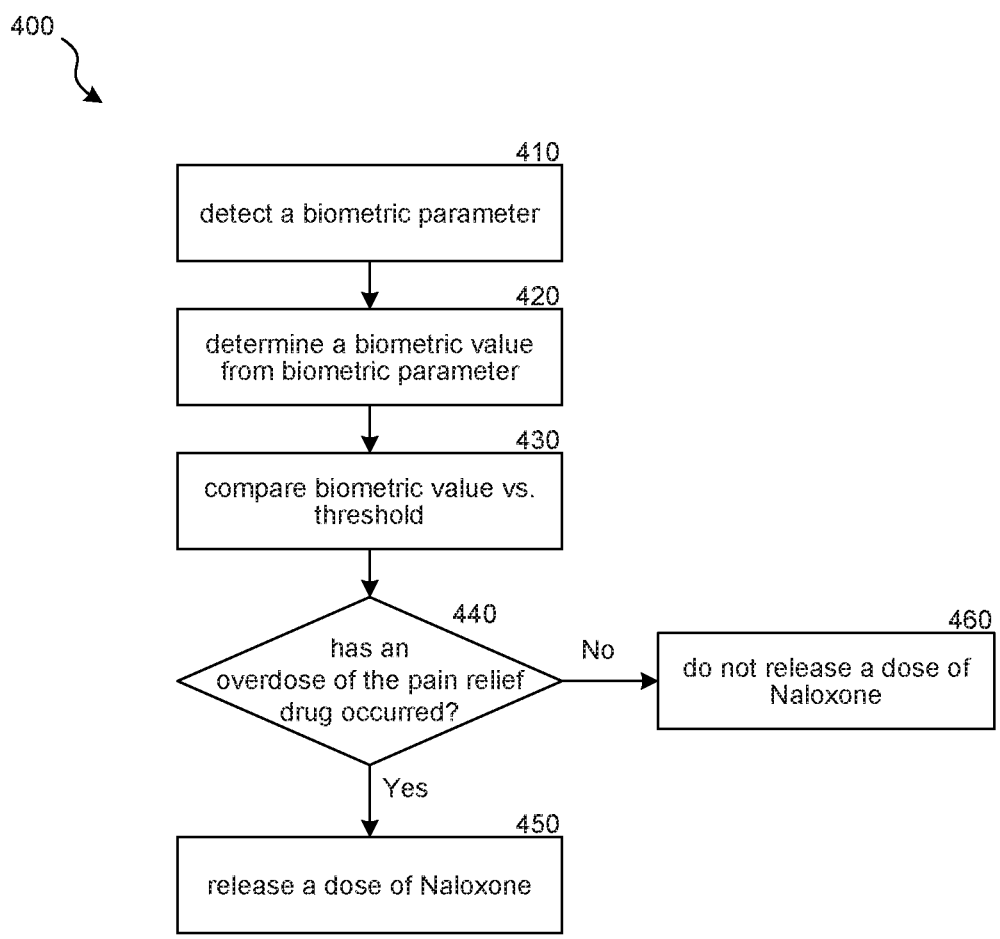
FIG. 4 is a block diagram illustrating a method of delivering a drug from the implantable drug delivery device to treat an opioid overdose in accordance with an embodiment of the present technology.

FIG. 4 is a block diagram illustrating a method of delivering a drug from the implantable drug delivery device to treat an opioid overdose in accordance with an embodiment of the present technology. As shown in FIG. 4, the method 400 includes detecting a biometric parameter (block 410). The biometric parameter is detected by delivering energy from the power source 140 to the sensors 120 which sense a response related to the biometric parameter. The method 400 also includes determining the biometric value from the detected biometric parameter (block 420). As described above with reference to FIGS. 1 and 3, one or more biometric values can be determined from the one or more biometric parameters. The biometric value is determined by the biometric parameter analysis program 335 of the controller 300 with reference to FIG. 3. Before detecting the biometric parameter (block 410), the method can include identifying a patient in need of the implantable drug delivery devices of the present technology and embodiments thereof and implanting the device into the patient in accordance with the present technology.

After determining the biometric value, the method 400 continues by comparing the biometric value against a threshold biometric value (block 430). For example, the comparison can include comparing the respiratory rate biometric value against a threshold respiratory rate biometric value and/or comparing the respiration biometric value against the respiration threshold biometric value. The comparison (block 430) is evaluated to determine if patient has overdosed on an opioid (block 440). Depending on the biometric parameter, the biometric value can be greater than, less than, or equal to the threshold biometric value to determine if the overdose occurred. For example, if the respiration biometric value is lower than the respiration threshold biometric parameter, an overdose has occurred. If the comparison indicates that the drug overdose occurred, a dose of naloxone is released from the reservoir 130 (block 450). However, if the comparison indicates that an overdose has not occurred, naloxone is not released from the reservoir 130 (block 460). For example, if the respiration biometric value is greater than or equal to the respiration threshold biometric parameter, the patient did not overdose. In some embodiments, the method 400 can continue by emitting or transmitting a signal from the signal emitter 150 or the signal transmitter 160 once the dose of naloxone is released (not shown).

Figure 5A:
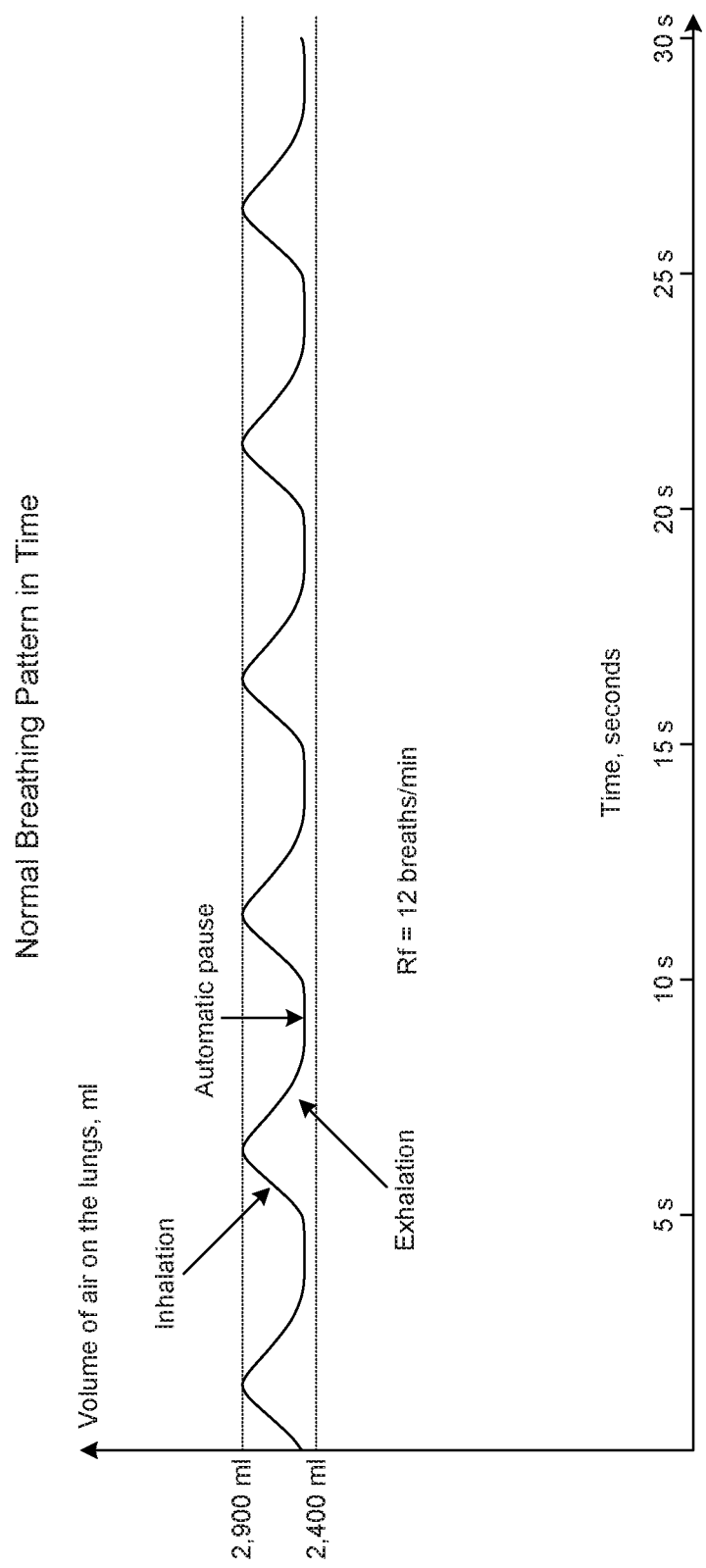
FIGS. 5A and 5B are illustrations of a normal human breathing pattern and an abnormal human breathing pattern over time, respectively.
Figure 5B:
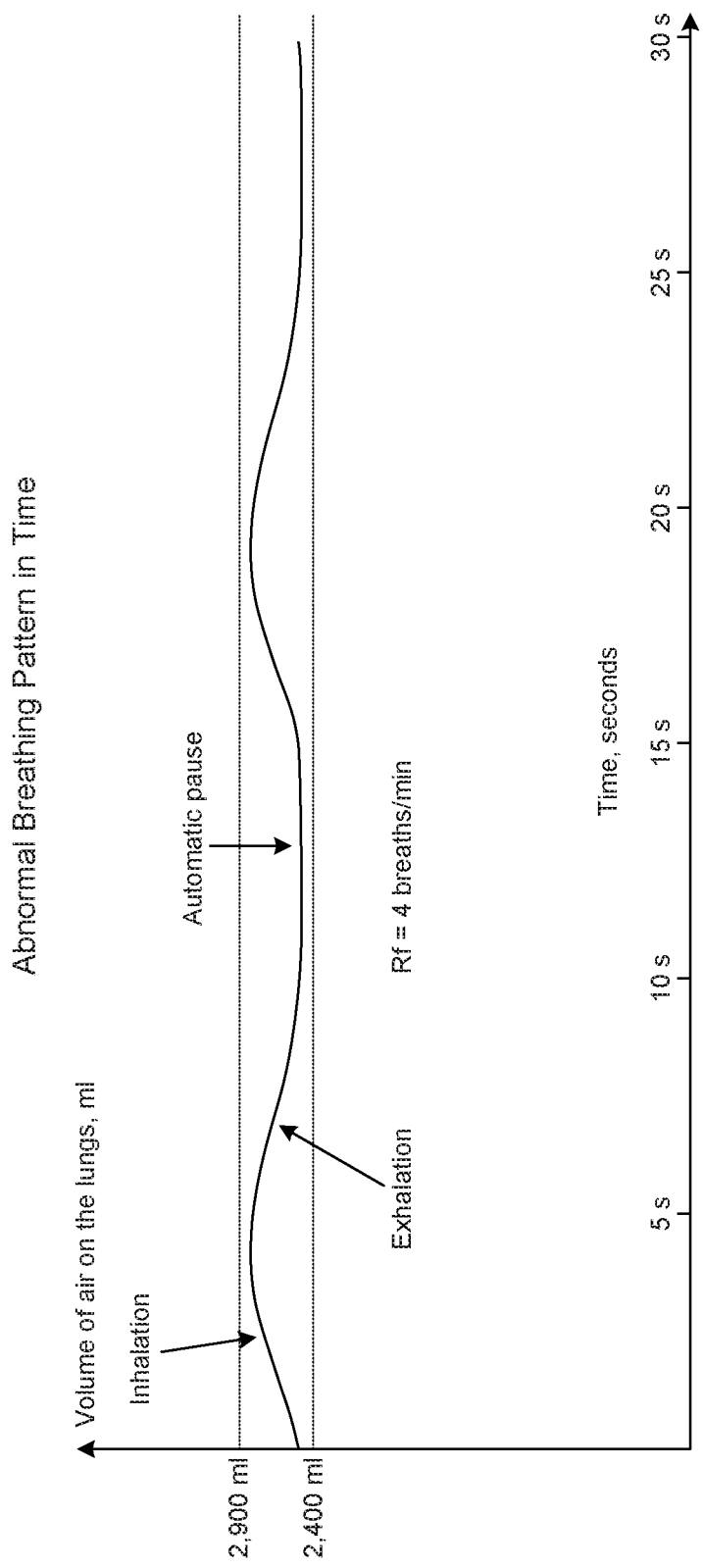

FIGS. 5A and 5B are illustrations of a normal human breathing pattern and an abnormal human breathing pattern over time, respectively. FIG. 5A illustrates a normal breathing pattern of an average, healthy human for a 30 second period. The respiration frequency (Rf) illustrated in FIG. 5A is 12 breaths per minute, and the Rf for average, healthy humans generally range from about 12 breaths per minute to about 16 breaths per minute. As illustrated, the functional residual capacity of the average, healthy human is about 2,400 ml (exhalation on the illustrated trace). The functional residual capacity is the amount of air remaining in the lungs after normal expiration. The functional residual capacity for average, healthy humans is generally from about 1,700 ml to about 2,600 ml. In addition, FIG. 5A illustrates a tidal volume of about 500 ml as inhalation to a volume of air on the lungs of 2,900 ml. The tidal volume refers to the amount of air inspired during normal, relaxed breathing (inhalation on the illustrated trace). Tidal volumes for average, healthy humans can range from about 400 ml to about 600 ml.

FIG. 5B illustrates an abnormal breathing pattern of a human experiencing respiratory depression. The Rf illustrated in FIG. 5B is 4 breaths per minute, and the range of abnormal Rfs for humans experiencing respiratory depression is from 0 breaths per minute to about 6 breaths per minute. As illustrated, the tidal volume for the human experiencing respiratory depression is about 300 ml but can range from about 1500 ml to about 350 ml. Compared to the normal breathing pattern illustrated in FIG. 5A, the human experiencing respiratory depression has a larger functional residual capacity and a lower tidal volume compared to the same human breathing normally. Based on FIGS. 5A and 5B, one embodiment of the device 100 shown in FIG. 1 releases the drug from the reservoir 130 when the controller 170 determines that the Rf is 4 breaths per minute or less, or in other embodiments when the Rf is 2 breaths per minute or less.

Figure 6:
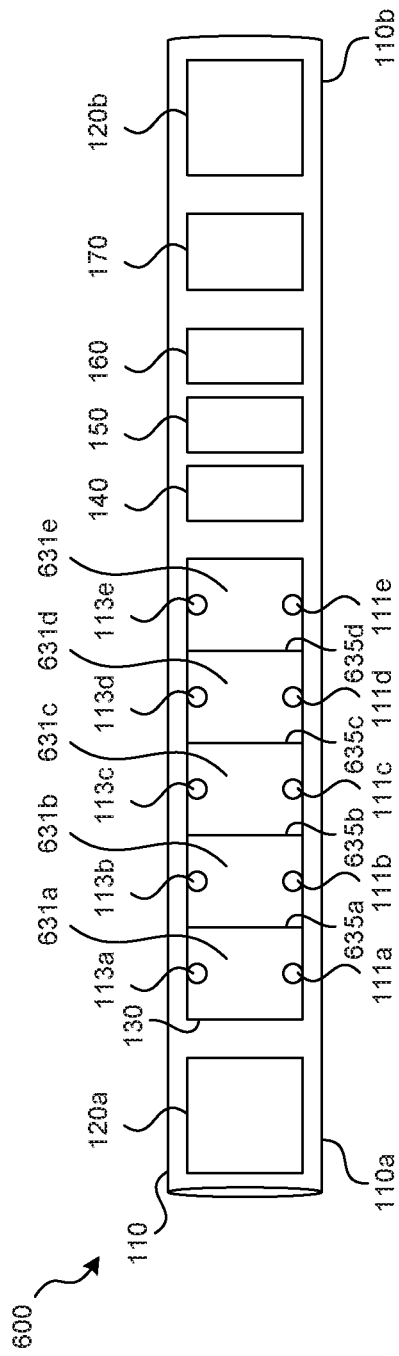
FIG. 6 is a schematic view of an implantable drug delivery device configured in accordance with another embodiment of the present technology.

II. Additional Embodiments of Implantable Drug Delivery Devices and Associated Methods FIG. 6 is an isometric view of an implantable drug delivery device configured in accordance with another embodiment of the present technology. The implantable drug delivery device 600 can include various features generally similar to those described above with reference to FIGS. 1-3, and like reference numbers refer to like components in FIGS. 1-6. In this embodiment, the implantable drug delivery device 600 includes a housing 110 carrying a first sensor 120a, a second sensor 120b, and a reservoir 130. In the embodiment of the implantable drug delivery device 600 shown in FIG. 6, the reservoir 130 is divided into a plurality of chambers 631a-631e (collectively "chambers 631") each fluidly separated from the other chambers 631 by a plurality of walls 635a-635d (collectively "walls 631"). The chambers 631 are each configured to carry a dose of a drug (e.g., naloxone) suitable to treat the opioid overdose, such as a 1 cc dose. The chambers 631 can also be configured to carry other volumes of naloxone doses described with reference to FIG. 1. In other embodiments, some of the chambers 631 carry naloxone and others carry a dose of a different pharmaceutical composition suitable to treat an overdose, such as flumazenil to reverse a benzodiazepine overdose or epinephrine to treat an allergic reaction. The chambers 631a-e are fluidly coupled to a corresponding outlet port 111a-111e, respectively, (collectively "outlet ports 111") and/or a pump 116 and needle 117 (not shown). Similar to FIG. 1, the outlet ports 111 extend from each chamber 631 of the reservoir 130 through the housing 110 fluidly coupling the outlet port 111 to the patient. In addition, the chambers 631a-e are fluidly coupled to a corresponding inlet port 113a-113e, respectively, (collectively "inlet ports 113") coupled to a re-sealable membrane (not shown).

Figure 7:
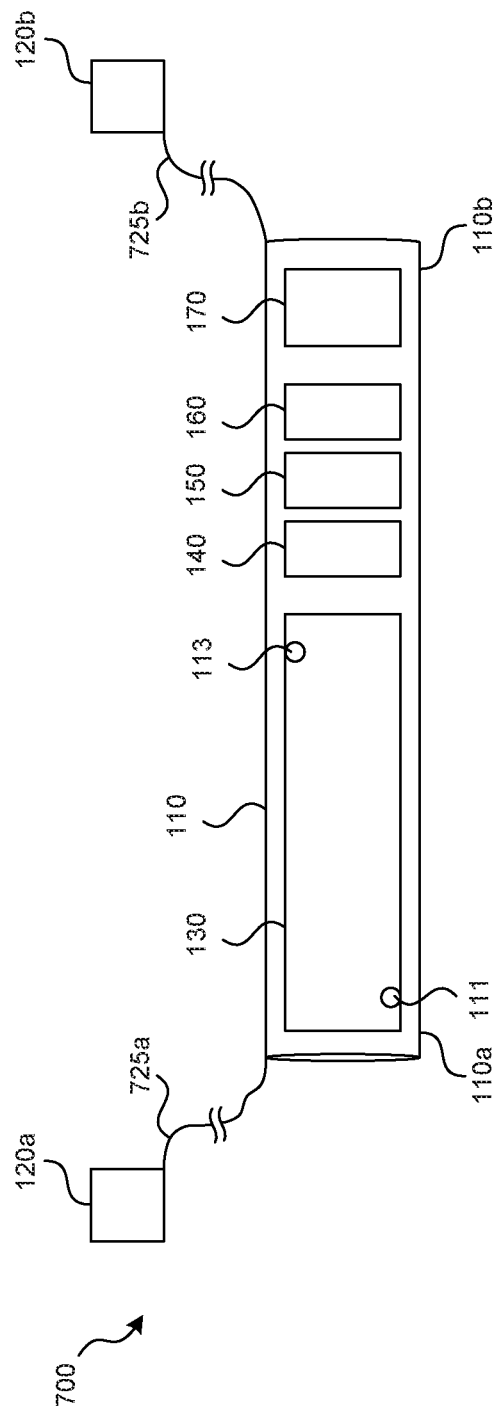
FIG. 7 is a schematic view of an implantable drug delivery device configured in accordance with yet another embodiment of the present technology.

FIG. 7 is an isometric view of an implantable drug delivery device configured in accordance with yet another embodiment of the present technology. The implantable drug delivery device 600 can include various features generally similar to those described above with reference to FIGS. 1-3 and 6, and like reference numbers refer to like components in FIGS. 1-7. In this embodiment, the implantable drug delivery device 700 includes a housing 110, a first sensor 120a, a second sensor 120b, and a reservoir 130. In the embodiment of the implantable drug delivery device 700 shown in FIG. 7, the first sensor 120a and the second sensor 120b are components of leads that can be positioned in the patient remotely from the housing 110 and coupled to the power source 140 by lead wires 725a and 725b (collectively "lead wires 725"). The lead wires 725 are insulated and can be configured as pairs of lead wires (not shown). In other embodiments, the sensors 120 can be wirelessly coupled to the power source 140.

Figure 8:
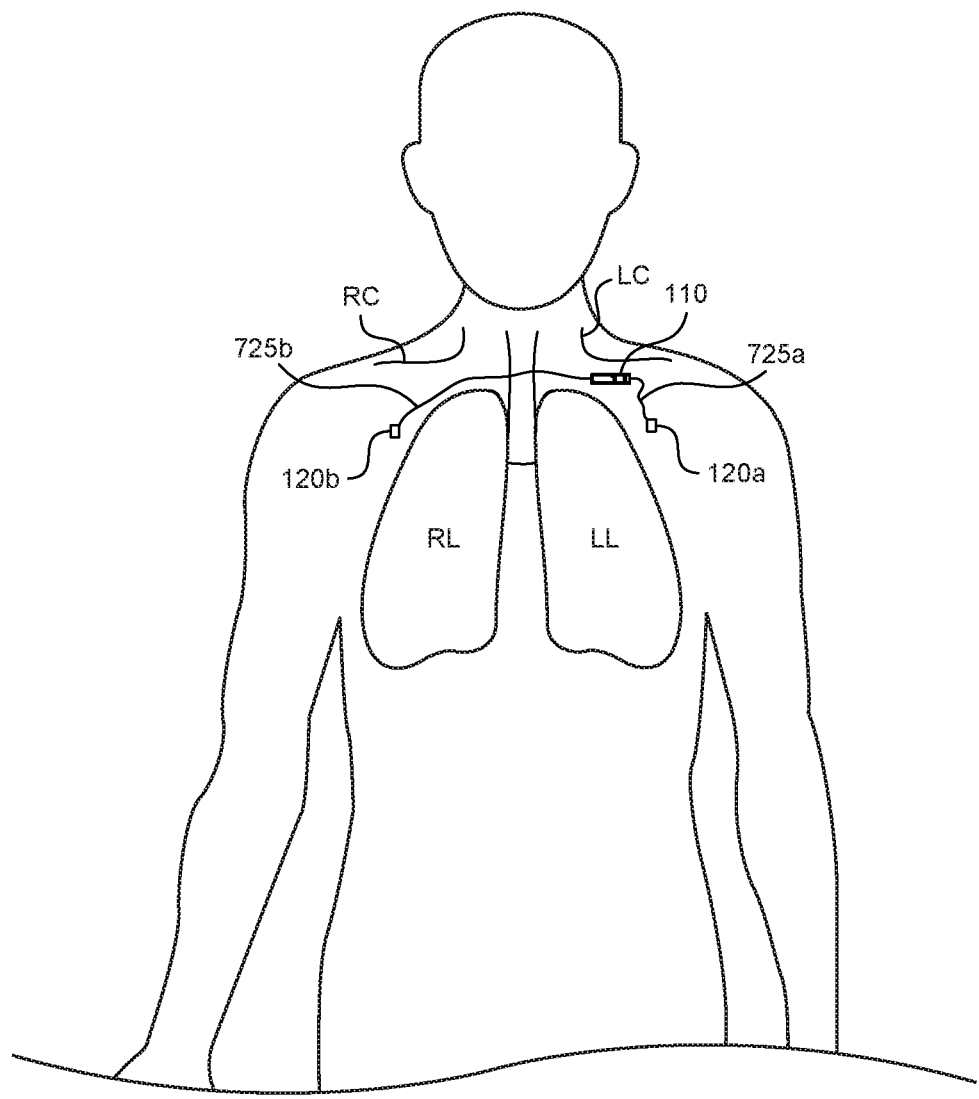
FIG. 8 is an anatomic view of the implantable drug delivery device of FIG. 7 implanted in a subclavicular space of a patient in accordance with an embodiment of the present technology.

FIG. 8 is an anatomic view of the implantable drug delivery device of FIG. 7 implanted within subclavicular space of a patient in accordance with an embodiment of the present technology. In the illustrated embodiment, the housing 110 is implanted into the patient through an incision made into the patient's subclavicular space, and the first lead (first sensor 120a and lead wires 725a) and second lead (second sensor 120b and lead wires 725b) are positioned in and/or on the patient apart from the housing 110 at locations suitable for sensing signals related to the biometric parameters. As illustrated, the first sensor 120a is positioned lateral to the left lung (LL) and the second sensor 120b is positioned lateral to the right lung (RL).

III. Implantable Drug Delivery Devices and Associated Systems and Environments FIG. 9 is a block diagram illustrating an overview of an environment 900 in which some implementations of the present technology can operate. The environment 900 can include one or more controllers 170/300 and one or more receiving devices, such as a phone 950 (cellular or telephone), a computer 960, and an emergency transponder 970. The phone 950 and/or the computer 960 can include memory and one or more applications configured to store and process data related to the patient's biometric parameter(s), biometric value(s), address, contact information for the patient's healthcare provider, family member or other party, and data related to whether the patient overdosed and/or whether the drug was released from the reservoir 130. These applications can be programmed to automatically dial a telephone number when the device determines that an overdose has occurred (e.g., block 440 in FIG. 4) and/or a drug is released from the reservoir 130 (e.g., block 450 in FIG. 4). The telephone number can be associated with the patient's healthcare provider, family member, and/or other party. In addition, the emergency transponder 970 is associated with an emergency response service, such as a dispatch center or an ambulance. The emergency transponder 970 can receive a transmitted signal from the signal transmitter 140 when the device determines that an overdose has occurred (e.g., block 440 in FIG. 4) and/or the drug is released from the reservoir 130 (e.g., block 450 in FIG. 4). The signal can automatically be transmitted to the emergency transponder 970.

The controllers 170/300 and receiving devices 950, 960, and 970 can operate in a networked environment using logical connections through a network 920 to one or more remote servers 930. The controller 170/300 and the receiving devices 950, 960, and 970 can be connected to the network 920 through network interfaces 915a-915d (collectively "interface 915"), such as by wired or wireless communication. While the connections between the controller 170/300, server 930, database 940, and the receiving devices phone 950, computer 960, and emergency transponder 970 are shown as separate connections, these connections can be any kind of network, including the network 920 or a separate network. Though each server can logically be a single server, server 930 (not shown) can each encompass multiple computing devices located at the same or at disparate physical locations. The server 930 can connect to a database 940 that can warehouse (e.g., store) information such as raw data (e.g., related to biometric parameters), calculated data (e.g., biometric values, threshold values), algorithms, other patient information, and/or other information necessary for the implementation of the devices and methods described above with respect to FIGS. 1-8.

IV. Additional Examples

The following examples are illustrative of several embodiments of the present technology:

1. An implantable drug delivery device, comprising:
 a housing configured to be implanted in a human;
 a reservoir carried by the housing, wherein the reservoir is configured to contain a drug;
 a first sensor and a second sensor each configured to detect a biometric parameter of the human associated with an overdose of an opioid; and
 a controller operatively coupled to the reservoir and the first and second sensors, wherein the controller is configured to receive signals detected by the first and second sensors related to the biometric parameter, determine whether the overdose of the opioid has occurred based on the signals received from the first and second sensors, and cause the drug in the reservoir to be delivered to the human if the overdose is detected.

2. The implantable drug delivery device of example 1, further comprising a pump operatively coupled to the reservoir and the controller, wherein the pump is activated by the controller to deliver the drug in the reservoir to the human when the overdose is detected.

3. The implantable drug delivery device of example 1 or example 2, further comprising an outlet port sealed with an outlet membrane and a release mechanism operatively coupled to the controller, wherein the release mechanism is activated by the controller and configured to remove at least a portion of the outlet membrane from the outlet port to deliver the drug in the reservoir to the human when the overdose is detected.

4. The implantable drug delivery device of any one of examples 1 to 3 wherein the drug is a composition comprising an opioid receptor antagonist, wherein the opioid receptor antagonist is naloxone.

5. The implantable drug delivery device of any one of examples 1 to 4 wherein the sensors are impedance sensors, inductor-capacitor oscillators, or a combination thereof.

6. The implantable drug delivery device of any one of examples 1 to 5 wherein the biometric parameter is a respiratory rate of the human.

7. The implantable drug delivery device of any one of examples 1 to 6 wherein the first and second sensors are carried by the housing or wirelessly coupled to the housing.

8. The implantable drug delivery device of any one of examples 1 to 7 wherein the first and second sensors are first and second leads, each lead comprising one or more contacts and one or more lead wires.

9. The implantable drug delivery device of any one of examples 1 to 8, further comprising a power source, wherein the power source is a battery or an accelerometer, and is configured to supply power to the sensors.

10. The implantable drug delivery device of any one of examples 1 to 9, further comprising a computer readable medium having instructions that, when executed by a processor, cause the device to:
 detect at least one of the biometric parameters by delivering energy to the sensors and sensing the biometric parameters;
 determine a biometric value from the detected biometric parameter;
 compare the biometric value against a threshold biometric value, and based on the comparison;
 determine whether the overdose of the opioid has occurred, and if the overdose has occurred;
 deliver the drug in the reservoir to the human.

11. The implantable drug delivery device of any one of examples 1 to 10 wherein the reservoir, the controller, and the computer readable medium are integral components of the housing 12. The implantable drug delivery device of any one of examples 1 to 11 wherein the device is coupled to a signal emitter or signal transmitter configured to emit or transmit a signal when the drug is released from the reservoir.

13. The implantable drug delivery device of any one of examples 1 to 12 wherein the emitted signal is an audible signal, a visual signal, or a combination thereof.

14. The implantable drug delivery device of any one of examples 1 to 13 wherein the transmitted signal is wirelessly transmitted to an external device.

15. The implantable drug delivery device of any one of examples 1 to 14 wherein the wirelessly transmitted signal is a telecommunications signal, a global positioning system signal, an audible signal, a visual signal, or a combination thereof.

16. The implantable drug delivery device of any one of examples 1 to 15 wherein the reservoir comprises a plurality of enclosed chambers each configured to contain the drug.

17. The implantable drug delivery device of any one of examples 1 to 16, further comprising a plurality of pumps operatively coupled to each of the chambers and the controller, wherein one or more pumps are activated by the controller to deliver the drug in one or more chambers to the human when the overdose is detected.

18. The implantable drug delivery device of any one of examples 1 to 17, further comprising a plurality of outlet ports each sealed with an outlet membrane and a plurality of release mechanisms operatively coupled to the controller, wherein each outlet port and each release mechanism are coupled to each chamber, and wherein one or more release mechanisms are activated by the controller and configured to remove at least a portion of one or more outlet membranes to deliver the drug in the chamber to the human when the overdose is detected.

19. The implantable drug delivery device of any one of examples 1 to 18, further comprising an inlet port coupled to the reservoir and sealed with a re-sealable membrane.

20. The implantable drug delivery device of any one of examples 1 to 19 wherein the reservoir is configured to be refilled with the drug through the re-sealable membrane if the drug is delivered to the human.

21. A non-transitory computer readable memory storing instructions that, when executed by a processor of a computing device, cause the computing device to perform operations for delivering a drug to a human from a reservoir of an implanted drug delivery device, the operations comprising:
  detect at least one biometric parameter of the human by delivering energy to sensors of the implanted device and sensing the biometric parameter;
  determine a biometric value from the detected biometric parameter;
  compare the biometric value against a threshold biometric value, and based on the comparison;
  determine whether an overdose of an opioid has occurred, and if the overdose has occurred;
  deliver the drug in the reservoir of the implanted device to the human.

22. A method of treating a human with an implanted drug delivery device, the method comprising:
  implanting the device into a subclavicular space of the human, wherein the device comprises—
    a housing configured to be implanted in the human,
    a first sensor and a second sensor each configured to detect a biometric parameter of the human associated with an overdose of a pain relief drug,
    a reservoir carried by the housing, wherein the reservoir is configured to contain a drug, and
    a controller operatively coupled to the reservoir and the first and second sensors, wherein the controller is configured to—
      receive signals detected by the first and second sensors related to the biometric parameter,
      determine whether the overdose of the opioid has occurred based on the signals received from the first and second sensors, and
      cause the drug in the reservoir to be delivered to the human if the overdose is detected;
  detecting the biometric parameter of the human by delivering energy to sensors and sensing the biometric parameter;
  determining a biometric value from the detected biometric parameter;
  comparing the biometric value against a threshold biometric value, and based on the comparison;
  determining whether the overdose of the opioid has occurred, and if the overdose has occurred;
  delivering the drug in the reservoir of the implanted device to the human.

V. Conclusion

From the foregoing, it will be appreciated that specific embodiments of the technology have been described herein for purposes of illustration, but well-known structures and functions have not been shown or described in detail to avoid unnecessarily obscuring the description of the embodiments of the technology. This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Certain aspects of the present technology may take the form of computer-executable instructions, including routines executed by a controller or other data processor. In some embodiments, the controller or other data processor is specifically programmed, configured, and/or constructed to perform one or more of these computer-executable instructions. Furthermore, some aspects of the present technology may take the form of data (e.g., non-transitory data) stored or distributed on computer-readable media, including magnetic or optically readable and/or removable computer discs as well as media distributed electronically over networks. Accordingly, data structures and transmissions of data particular to aspects of the present technology are encompassed within the scope of the present technology. The present technology also encompasses methods of both programming computer-readable media to perform particular steps and executing the steps.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms may also include the plural or singular term, respectively. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

I claim:

1. An implantable drug delivery device, comprising:
a housing configured to be implanted in a human, the housing having an outer surface and an outlet port through the housing configured to dispense a drug to the human at the outer surface of the housing;
a reservoir carried by the housing, wherein the reservoir is configured to contain the drug and is fluidically coupled to the outlet port;
a first sensor and a second sensor each configured to detect a biometric parameter of the human associated with an overdose of an opioid;
a controller operatively coupled to the reservoir, the first sensor and the second sensor, wherein the controller is configured to receive signals detected by the first sensor and the second sensor related to the biometric parameter, determine whether the overdose of the opioid has occurred based on the signals received from the first sensor and the second sensor, and cause the drug in the reservoir to be delivered to the human if the overdose is detected; and
a drug release mechanism sealing the outlet port and configured to prevent release of the drug until the overdose has been determined.

2. The implantable drug delivery device of claim 1, further comprising a pump operatively coupled to the reservoir and the controller, wherein the pump is activated by the controller to deliver the drug in the reservoir to the human when the overdose is detected.

3. The implantable drug delivery device of claim 1 wherein the drug is a composition comprising an opioid receptor antagonist, wherein the opioid receptor antagonist is naloxone.

4. The implantable drug delivery device of claim 1 wherein the first sensor and the second sensor are impedance sensors, inductor-capacitor oscillators, or a combination thereof.

5. The implantable drug delivery device of claim 1 wherein the biometric parameter is the respiratory rate of the human.

6. The implantable drug delivery device of claim 1 wherein the first sensor and the second sensor are carried by the housing or wirelessly coupled to the housing.

7. The implantable drug delivery device of claim 1 wherein the first sensor is a first lead and the second sensor is a second lead, each of the first lead and the second lead comprising one or more contacts and one or more lead wires.

8. The implantable drug delivery device of claim 1, further comprising a power source, wherein the power source is a battery or an accelerometer, and is configured to supply power to the first sensor and the second sensor.

9. The implantable drug delivery device of claim 1, further comprising a computer readable medium having instructions that, when executed by a processor, cause the device to:
detect at least one of the biometric parameters by delivering energy to the first sensor and the second sensor and sensing the biometric parameters;
determine a biometric value from the detected biometric parameter;
compare the biometric value against a threshold biometric value, and based on the comparison;
determine whether the overdose of the opioid has occurred, and if the overdose has occurred;
deliver the drug in the reservoir to the human.

10. The implantable drug delivery device of claim 9 wherein the reservoir, the controller, and the computer readable medium are integral components of the housing.

11. The implantable drug delivery device of claim 1 wherein the device is coupled to a signal emitter or a signal transmitter configured to emit or transmit a signal when the drug is released from the reservoir.

12. The implantable drug delivery device of claim 11 wherein the transmitted signal is wirelessly transmitted to an external device.

13. The implantable drug delivery device of claim 12 wherein the wirelessly transmitted signal is a telecommunications signal, a global positioning system signal, an audible signal, a visual signal, or a combination thereof.

14. The implantable drug delivery device of claim 11 wherein the emitted signal is an audible signal, a visual signal, or a combination thereof.

15. The implantable drug delivery device of claim 1 wherein the reservoir comprises a plurality of enclosed chambers each configured to contain the drug.

16. The implantable drug delivery device of claim 15, further comprising a plurality of pumps operatively coupled to the controller and each of the enclosed chambers respectively, wherein one or more of the pumps of the plurality of pumps are activated by the controller to deliver the drug from the one or more of the plurality of enclosed chambers to the human when the overdose is detected.

17. The implantable drug delivery device of claim 15, further comprising a plurality of outlet ports each sealed with an outlet membrane and a plurality of release mechanisms operatively coupled to the controller, wherein each outlet port of the plurality of outlet ports and each release mechanism of the plurality of release mechanisms are coupled respectively to each chamber of the plurality of enclosed chambers, and wherein one or more release mechanisms of the plurality of release mechanisms are activated by the controller and configured to remove at least a portion of one or more outlet membranes to deliver the drug from a respective one or more enclosed chambers of the plurality of enclosed chambers to the human when the overdose is detected.

18. The implantable drug delivery device of claim 1, further comprising an inlet port coupled to the reservoir and sealed with a re-sealable membrane.

19. The implantable drug delivery device of claim 18 wherein the reservoir is configured to be refilled with the drug through the re-sealable membrane if the drug is delivered to the human.

20. The implantable drug delivery device of claim 1 wherein the outlet port comprises a hole through the housing and the drug release mechanism comprises a membrane covering the hole.

21. The implantable drug delivery device of claim 1 wherein the drug release mechanism comprises an outlet membrane and the outlet port is sealed by the outlet membrane such that the outlet membrane is configured to prevent release of the drug.

22. The implantable drug delivery device of claim 21 wherein the outlet membrane is in the outlet port.

23. An implantable drug delivery device, comprising:

a housing configured to be implanted in a human, the housing having an outlet port that extends through the housing, wherein the outlet port defines a flow path for dispensing a drug such that the drug is released to the human at the housing;

a reservoir carried by the housing, wherein the reservoir is configured to contain the drug and is fluidically coupled to the outlet port;

a first sensor and a second sensor each configured to detect a biometric parameter of the human associated with an overdose of an opioid; and a controller operatively coupled to the reservoir, the first sensor and the second sensor, wherein the controller is configured to receive signals detected by the first sensor and the second sensor related to the biometric parameter, determine whether the overdose of the opioid has occurred based on the signals received from the first sensor and the second sensor, and cause the drug in the reservoir to be delivered to the human if the overdose is detected; and a drug release mechanism sealed to and within the outlet port that is configured to prevent release of the drug until the overdose has been determined.

24. The implantable drug delivery device of claim 23 wherein the drug release mechanism comprises a membrane in the outlet port.

* * * * *